United States Patent [19]

van Andel

[11] Plant 5,207

[45] Mar. 20, 1984

[54] ALSTROEMERIA NAMED STALILAS

[75] Inventor: Jacob van Andel, Aalsmeer, Netherlands

[73] Assignee: B. V. Handelskwekerij, M. C. van Staaveren, Aalsmeer, Netherlands

[21] Appl. No.: 416,841

[22] Filed: Sep. 13, 1982

[51] Int. Cl.[3] ..... A01H 5/00

[52] U.S. Cl. ..... Plt./68

[58] Field of Search ..... Plt./68

*Primary Examiner*—James R. Feyrer

*Attorney, Agent, or Firm*—Chas. W. Rummler

[57] ABSTRACT

A new alstroemeria variety, originated as a seedling in greenhouse at Aalsmeer, Holland, resulting from my crossing of selected greenhouse varieties, grown for breeding purposes at Aalsmeer, with the object of developing new flower color in plants having good flowering characteristics during the fall, winter and spring months. This particular seedling was selected for propagation and testing because of its very lovely light purple coloring and its profuse production of blooms borne on relatively long and strong peduncles. Propagation of this cultivar through successive generations at Aalsmeer, by division of root stocks, has demonstrated that its novel characteristics hold true from generation to generation and appear to be firmly fixed.

1 Drawing Figure

DESCRIPTION OF THE DRAWING

My new alstroemeria variety is illustrated by the accompanying photographic drawing which, in full color, shows the inflorescence of this plant as it appears at the top of the flowering stem, the colors shown being as nearly true as is reasonably possible to obtain by conventional professional photographic processing techniques.

DESCRIPTION OF THE NEW PLANT

The following is a detailed description of my new variety of alstroemeria plant with color designations according to the R.H.S. Colour Chart of The Royal Horticultural Society of London, England, the photograph having been made in greenhouse and showing springtime flowering.

THE PLANT

Origin: Seedling.

Seed parent: Stock No. 6,288 B.

Pollen parent: Stock No. 6,261 L.

The parent plants are stock varieties maintained for breeding purposes and identified by assigned numbers recorded in permanent greenhouse records.

Classification:

*Botanic.*—Alstroemeria.

*Commercial.*—Alstroemeria Hybrid.

Form: A tall, slender and erect flowering stalk with flower bearing branches in compound umbel arrangement at its top.

Height: About 150 to 200 cm.

Growth: Vigorous and upright with good strength.

Root stock: Tuberous. The tubers bear numerous buds during the year from which the flower stalks grow in various stages of development in the course of the blooming seasons.

Foliage:

*Quantity.*—Medium with about 20 to 30 leaves per stem, the number being influenced by the season.

Leaf shape: Elliptic.

Texture: Soft.

Color:

*Upper side.*—Dark Green.

*Under side.*—Medium Green.

Rizomes: The rizomes are white in color, the size varying with the seasons.

THE BUD

Form: Pear-shaped.

Size: Medium with a diameter about 1 cm. and length of about 2.5 cm.

Opening: The bud opens slowly; there is no calyx, and the six petals are a perianth.

Peduncle:

*Length.*—Approximately 10 cm.

*Character.*—Rigid, making an angle of approximately 60 degrees with the stem.

THE FLOWER

Blooming habit: Recurrent from fall through winter and spring with profuse and substantially continuous blossoming during each season of blooming.

Flower size: Medium.

*Diameter.*—About 5.5 to 6.0 cm.

*Depth.*—About 4 cm.

Borne: Singly on a relatively long peduncle.

Shape: Cup-shaped and generally funnel-like.

Petalage;

*Number of petals.*—6.

*Arrangement.*—Two circles of 3 petals each.

*Form.*—Broad ovate with slightly serrated apex.

Texture: Soft.

Appearance: Shiny.

Color:

*Outer petals.*—71C in the main body and 72C-D at the base.

*Reverse side.*—71C-D and 67A-71B at the petal tips.

*Inside petals.*—Body 71C-D with inner third of some petals being 155B, the entire petal being covered with short longitudinal dark browm pencil stripes.

Persistence: Generally the flowers hang on and dry.

Peduncle: Sturdy and upright, the length depending upon age during the blooming season.

Color: Green.
Fragrance: None.
Lasting quality:
*On the plant.*—16 to 20 days.
*As a cut flower.*—10 to 14 days.

REPRODUCTIVE ORGANS

Stamens:
*Number.*—Six, one opposite each petal.
*Anthers.*—Length — approximately 7 mm.
*Filaments.*—Length — about 4 cm.
*Color.*—Purple.
Pistils:

*Number.*—one.
*Length.*—About 6 mm.
*Color.*—Purple.
Stigma:
*Color.*—Purple-red.

I claim:

1. The new and distinct alstroemeria cultivar substantially as herein shown and described, characterized by the distinctive light purple coloration of the flowers with white coloring on about the inner third of the inside petals, and by the sturdy and relatively long peduncle for each of the flowers.

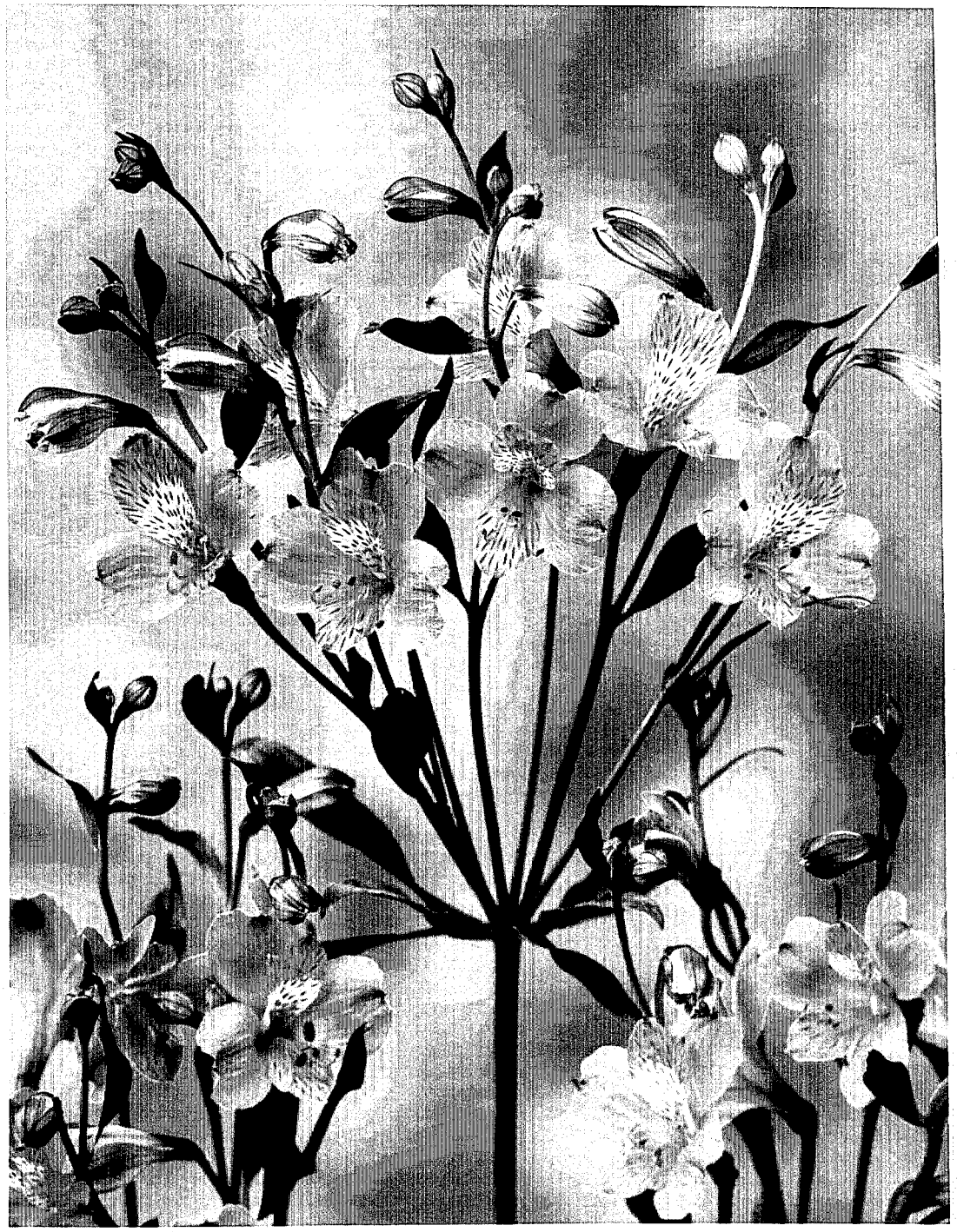

* * * * *